US010519422B2

(12) United States Patent
Takahashi et al.

(10) Patent No.: US 10,519,422 B2
(45) Date of Patent: Dec. 31, 2019

(54) METHOD OF PRODUCING HUMAN RETINAL PIGMENT EPITHELIAL CELLS

(75) Inventors: Masayo Takahashi, Hyogo (JP); Satoshi Okamoto, Hyogo (JP); Noriko Sakai, Hyogo (JP)

(73) Assignee: RIKEN, Wako (JP)

( * ) Notice: Subject to any disclaimer, the term of this patent is extended or adjusted under 35 U.S.C. 154(b) by 480 days.

(21) Appl. No.: 13/408,642

(22) Filed: Feb. 29, 2012

(65) Prior Publication Data
US 2013/0224156 A1  Aug. 29, 2013

(51) Int. Cl.
C12N 5/079 (2010.01)
A61K 35/30 (2015.01)

(52) U.S. Cl.
CPC ............ *C12N 5/0621* (2013.01); *A61K 35/30* (2013.01); *C12N 2501/115* (2013.01); *C12N 2501/40* (2013.01); *C12N 2501/415* (2013.01); *C12N 2501/727* (2013.01); *C12N 2506/45* (2013.01); *C12N 2533/32* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 7,541,186 B2 | 6/2009 | Reh et al. | |
| 7,736,896 B2 | 6/2010 | Klimanskaya et al. | |
| 2010/0105137 A1* | 4/2010 | Takahashi | C12N 5/0621 435/377 |

FOREIGN PATENT DOCUMENTS

| | | |
|---|---|---|
| EP | 1783205 A1 | 5/2007 |
| EP | 2128244 A1 | 12/2009 |
| WO | WO 2004/090110 A1 | 10/2004 |
| WO | WO 2005/123902 A1 | 12/2005 |
| WO | WO 2008/087917 A1 | 7/2008 |
| WO | WO 2009/051671 * | 4/2009 |
| WO | WO 2009051671 A1 * | 4/2009 |

OTHER PUBLICATIONS

Kawasaki et al., Proc. Nat'l. Acad. Sci. USA 99(3): 1580-1585 (2002).*
Fusaki et al., Proc. Jpn. Acad., Ser. B, 85(8): 348-362 (2009).
Ikeda et al., Proc. Natl. Acad. Sci. USA, 102(32): 11331-11336 (2005).
Maminishkis et al., *Invest. Ophthalmol. Vis. Sci.*, 47(8): 3612-3624 (2006).
Okita et al., *Nature Methods*, 8(5): 409-412 (2011) (with "Online Methods," 2 pgs.).
Osakada et al., *Nature Biotechnology*, 26(2): 215-224 (2008).
Osakada et al., *J. Cell Sci.*, 122(17): 3169-3179 (2009).
Geling et al., *EMBO Reports*, 3(7): 688-694 (2002).
Hirano et al., *Developmental Dynamics*, 228: 664-671 (2003).
Jadhav et al., *Development*, 133: 913-923 (Mar. 1, 2006).
Lamba et al., *Proc. Natl. Acad. Sci. USA*, 103(34): 12769-12774 (Aug. 22, 2006).
Livesey et al., *Nature Reviews Neuroscience*, 2: 109-118 (2001).
Mandai et al., *Koseirodosho Nanjisei Shikkan Kokufuku Kenkyu Jigyo Momaku Myakurakumaku, Shishinkei Ishukusho Chosa Kenkyuhan, Heisei 18 Nendo Hankaigi Program*, p. 70 (Jan. 12, 2007).
Nelson et al., *Developmental Neuroscience*, 28: 128-141 (Jan. 1, 2006).
Nelson et al., *Developmental Biology*, 304(2): 479-498 (Apr. 15, 2007).
Ooto et al., *Investigative Ophthalmology & Visual Science*, 44(6): 2689-2693 (Jun. 2003).
Takahashi, "Preparation of transplantable retinal cells from human ES cells," *Igaku-no-Ayumi*, 220(2): 143-146 (2007).
Ueno et al., *PNAS*, 103(25): 9554-9559 (2006).
Watanabe et al., *Nature Neuroscience*, 8(3): 288-296 (Mar. 2005).
Weihofen et al., *J. Biol. Chem.*, 278(19): 16528-16533 (2003).
Yaron et al., *Development*, 133: 1367-1378 (2006).
Young et al., *Neuron*, 41: 867-879 (2004).
European Patent Office, Supplementary European Search Report in European Patent Application No. 08703169.6 (dated Apr. 3, 2012).
Japanese Patent Office, International Search Report in International Patent Application No. PCT/JP2008/050305 (dated Apr. 22, 2008).
Japanese Patent Office, Office Action in Japanese Patent Application No. 2008-554025 (dated Dec. 4, 2012).
Japanese Patent Office, Office Action in Japanese Patent Application No. 2008-554025 (dated Sep. 17, 2013).
International Bureau of WIPO, International Preliminary Report on Patentability in International Patent Application No. PCT/JP2008/050305 (dated Jul. 21, 2009).
Chung et al., "Human Embryonic Stem Cell Lines Generated without Embryo Destruction," *Cell Stem Cell*, 2(2): 113-117 (Feb. 2008).
Eiraku et al., "Self-organizing optic-cup morphogenesis in three-dimensional culture," *Nature*, 472(7341): 51-56 (Apr. 7, 2011).
Wikipedia, "Embryoid body," downloaded from http://en.wikipedia.org/wiki/Embryoid body (Jul. 24, 2014).
European Patent Office, Office Action in European Patent Application No. 08703169.6 (dated Nov. 18, 2013).

(Continued)

*Primary Examiner* — Erin M. Bowers
(74) *Attorney, Agent, or Firm* — Leydig, Voit & Mayer, Ltd.

(57) ABSTRACT

The invention relates to a method of producing a retinal pigment epithelial cell from a human pluripotent stem cell, and a method of treating or preventing a retinal disease by using the produced cell. The retinal pigment epithelial cell is prepared by (a) inducing differentiation of a human pluripotent stem cell into a pigment cell by adhesion cultivation of a human pluripotent stem cell in a medium containing a Nodal signal inhibitor and a Wnt signal inhibitor in the absence of a feeder cell to give a culture containing the pigment cell, (b) subjecting the obtained culture to further adhesion culture to give a culture containing a pigment cell colony, and (c) isolating the pigment cell from the obtained culture and culturing the cell to give a retinal pigment epithelial cell.

7 Claims, No Drawings
Specification includes a Sequence Listing.

(56) References Cited

OTHER PUBLICATIONS

Kurosawa, "Methods for Inducing Embryoid Body Formation: In Vitro Differentiation System of Embryonic Stem Cells", *Journal of Bioscience and Bioengineering*, 103(5): 389-398 (2007).
U.S. Appl. No. 12/523,444, filed Oct. 13, 2009.

* cited by examiner

```
                        SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic F primer for human RPE65

<400> SEQUENCE: 1
tccccaatac aactgccact                                          20

<210> SEQ ID NO 2
<211> LENGTH: 20
<212> TYPE: DNA
<213> ORGANISM: Artificial Sequence
<220> FEATURE:
<223> OTHER INFORMATION: Synthetic R primer for human RPE65

<400> SEQUENCE: 2
ccttggcatt cagaatcagg                                          20

<210> SEQ ID NO 3
<211> LENGTH: 20
<212> TYPE: DNA
<213> ORGANISM: Artificial Sequence
<220> FEATURE:
<223> OTHER INFORMATION: Synthetic F primer for human CRALBP

<400> SEQUENCE: 3
gagggtgcaa gagaaggaca                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic R primer for human CRALBP

<400> SEQUENCE: 4
tgcagaagcc attgatttga                                          20
```

```
<210> SEQ ID NO 5
<211> LENGTH: 20
<212> TYPE: DNA
<213> ORGANISM: Artificial Sequence
<220> FEATURE:
<223> OTHER INFORMATION: Synthetic F primer for human MERTK

<400> SEQUENCE: 5
tccttggcca tcagaaaaag                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic R primer for human MERTK

<400> SEQUENCE: 6
catttgggtg gctgaagtct                                               20

<210> SEQ ID NO 7
<211> LENGTH: 19
<212> TYPE: DNA
<213> ORGANISM: Artificial Sequence
<220> FEATURE:
<223> OTHER INFORMATION: Synthetic F primer for human BEST1

<400> SEQUENCE: 7
tagaaccatc agcgccgtc                                                19

<210> SEQ ID NO 8
<211> LENGTH: 21
<212> TYPE: DNA
<213> ORGANISM: Artificial Sequence
<220> FEATURE:
<223> OTHER INFORMATION: Synthetic R primer for human BEST1

<400> SEQUENCE: 8
tgagtgtagt gtgtatgttg g                                             21
```

METHOD OF PRODUCING HUMAN RETINAL PIGMENT EPITHELIAL CELLS

TECHNICAL FIELD

The present invention relates to a method of producing a retinal pigment epithelial cell from a human pluripotent stem cell, and a medical use of a retinal pigment epithelial cell obtainable by said production method.

BACKGROUND ART

As a method of preparing retinal pigment epithelial cells from human pluripotent stem cells, (i) a method in which cells are left to spontaneously develop into retinal pigment epithelial cells by extracting bFGF from a medium component for culturing human ES cells (spontaneous differentiation method), (ii) a method based on coculture with mouse mesenchymal cell line PA6 (SDIA method), (iii) a method in which SFEB method including culturing human ES cells as a floating aggregate in a serum-free medium is combined with Nodal signal inhibitor Dkk1 and Wnt signal inhibitor LeftyA (SFEB/DL method) and the like are known. However, (i) spontaneous differentiation method (U.S. Pat. No. 7,736,896 etc.) is associated with a problem of marked variation in the differentiation induction efficiency depending on the line of human ES cell and the like to be a starting material. (ii) SDIA method (Proc Natl Acad Sci USA. 2002 Feb. 5 99(3) etc.) is feared to cause a safety problem due to virus contamination etc. resulting from the use of a cell of a mouse, which is an xenogeneic animal, even though the differentiation induction efficiency does not rely much on the difference in the line of human ES cell and the like to be used, and constant differentiation induction into retinal pigment epithelial cell is possible. (iii) SFEB/DL method (PNAS Aug. 9, 2005 vol. 102 no. 32 11331-11336, Nat Biotechnol. 2008 Feb. 26(2)215-24 etc.) reported thereafter is more suitable as a method for producing cells for cell transplantation therapy, as compared to the aforementioned (i) and (ii), since it shows comparatively small variation in the differentiation induction efficiency among human ES cell lines, and does not require separate preparation of xenogeneic cells.

During the process of examining clinical application of the SFEB/DL method, the present inventors have found that differentiation inducing factors including recombinant protein Dkk1 corresponding to the Nodal signal inhibitor, and recombinant protein LeftyA corresponding to the Wnt signal inhibitor can be substituted by low-molecular-weight compounds CKI-7 and SB-431542, respectively (SFEB/CS method; WO2008/087917), and established a method of stably and economically ensuring the supply of a differentiation inducing factor. However, the SFEB/CS method requires a long term of about 40 days before emergence of pigment cells from pluripotent stem cells (Journal of Cell Science 2009 Sep. 1 122(Pt 17) 3169-79), thus posing a major problem in the quality management and economical aspect. In addition, a floating culture has a problem in that the cells are easily lost during medium exchange, thus causing a decrease in the yield of the final product. Furthermore, for transplantation use, a method capable of stably obtaining a population of highly pure retinal pigment epithelial cells by a simple method has been desired

DISCLOSURE OF THE INVENTION

An object of the present invention is to provide a method that enables stable induction of differentiation of pluripotent stem cells into retinal pigment epithelial cells without using xenogeneic cells, and can shorten the term of differentiation induction.

Another object of the present invention is to provide a method that can easily remove unnecessary cells from the culture obtained by induction of differentiation of pluripotent stem cells into retinal pigment epithelial cells in the aforementioned method, and can improve work efficiency of the purification of the retinal pigment epithelial cells.

In an attempt to solve the aforementioned problems, the present inventors have conducted intensive studies of the conditions for inducing differentiation into retinal pigment epithelial cells using a medium containing a Nodal signal inhibitor and a Wnt signal inhibitor, and found that differentiation can be induced even under adhesion culture conditions, though conventional essential conditions include formation of floating aggregates, and that the term before emergence of pigment cells from pluripotent stem cells can be shortened drastically.

The present inventors have also found that adhesion culture in a culture vessel coated with gelatin, which is a material approved for clinical use, facilitates application to a cell transplantation therapy, and particularly that the workability of the purification of retinal pigment epithelial cells can be improved since pigment cells obtained by differentiation induction in a culture vessel coated with polylysine and gelatin has a smooth surface to which unnecessary cells are difficult to attach, and floating aggregate of pigment cells facilitate detachment of unnecessary cells.

Further studies based on the above findings have resulted in the completion of the present invention.

Accordingly, the present invention provides a method of producing a retinal pigment epithelial cell from a human pluripotent stem cell, which includes (a) a step of inducing differentiation of a human pluripotent stem cell into a pigment cell by adhesion cultivation of the human pluripotent stem cell in a medium containing a Nodal signal inhibitor and a Wnt signal inhibitor in the absence of a feeder cell to give a culture containing the pigment cell, (b) a step of subjecting the obtained culture to further adhesion culture to give a culture containing a pigment cell colony, and (c) a step of isolating the pigment cell from the obtained culture and culturing the cell to give the retinal pigment epithelial cell. The adhesion culture in the aforementioned step (a) may be performed using a culture vessel coated with gelatin, or a culture container coated with polylysine and gelatin may also be used. In the aforementioned step (a), SB-431542 can be used as a Nodal signal inhibitor and CKI-7 can be used as a Wnt signal inhibitor. The medium in the aforementioned step (a) may be a serum-free medium. The aforementioned step (c) may include (c-1) a step of subjecting the obtained culture to floating culture and (c-2) a step of isolating the pigment cell from the obtained culture, subjecting the pigment cell to adhesion culture, and to selective passage to give a retinal pigment epithelial cell.

In addition, the present invention also relates to a treatment method of a retinal disease in a human, comprising administering an effective amount of a retinal pigment epithelial cell produced by the aforementioned method to the human. As the aforementioned retinal disease, age-related macular degeneration, angioid streaks, high myopia (degenerative myopia), idiopathic neovascular maculopathy, retinitis pigmentosa, Stargardt's disease, Best's disease and choroideremia and the like can be mentioned.

BEST MODE FOR CARRYING OUT THE INVENTION

The method of producing a retinal pigment epithelial cell from a human pluripotent stem cell of the present invention comprises (a) a step of inducing differentiation of the human pluripotent stem cell into a pigment cell by adhesion cultivation of the human pluripotent stem cell in a medium containing a Nodal signal inhibitor and a Wnt signal inhibitor in the absence of a feeder cell to give a culture containing the pigment cell, (b) a step of subjecting the obtained culture to further adhesion culture, and (c) a step of isolating the pigment cell from the obtained culture and culturing the cell to give a retinal pigment epithelial cell.

In the present specification, the "conventional SFEB method" means a method of inducing differentiation of a human pluripotent stem cell into a retinal pigment epithelial cell by culturing the human pluripotent stem cell as a floating aggregate in a serum-free medium containing a Nodal signal inhibitor and a Wnt signal inhibitor, in the absence of a feeder cell, including SFEB/DL method and SFEB/CS method.

The "pigment cell" means a cell that produces and has a melanin pigment. In a preferable embodiment, the pigment cell appears brown to black. In one embodiment, a cell having a pigment of other color such as white, yellow and the like, which is seen in the production step in the present invention, is an unnecessary cell and excluded from the pigment cells.

Step (a) Differentiation Induction

Step (a) comprises inducing differentiation of a human pluripotent stem cell into a pigment cell by adhesion cultivation of the human pluripotent stem cell in a medium containing a Nodal signal inhibitor and a Wnt signal inhibitor in the absence of a feeder cell to give a culture containing the pigment cell.

In the present invention, step (a) is characterized in that differentiation of a human pluripotent stem cell into a pigment cell is induced under adhesion culture conditions instead of the floating culture conditions employed in conventional SFEB methods. In conventional SFEB methods, moreover, pluripotent stem cells form a floating aggregate, whereas in the method of the present invention, pluripotent stem cells form widespread laminated layers which are adhered onto the culture vessel. Therefore, they are different in the cell forms during differentiation induction. According to the present invention, differentiation induction is performed by adhesion culture, which drastically shortens the time up to the appearance of a pigment cell from a pluripotent stem cell. As a result, the present invention affords a superior effect in that the time period before obtaining the object cell can be shortened in the production of retinal pigment epithelial cell, which in turn reduces the production cost. Although the reason for the shortened time of differentiation induction is not clear, it is possible that differences in the culture environment and cell form during differentiation induction exert some influence on the promotion of the differentiation of a pluripotent stem cell.

Pluripotent stem cell is not particularly limited as long as it has self-replication competence and pluripotency and, for example, embryonic stem cells (ES cells), induced pluripotent stem cells (iPS cells), nuclear transfer ES cells (ntES cells), parthenogenetic embryo-derived ES cells (pES cells), and cells having modified genes of these cells and the like can be used alone or a plurality thereof can be used in combination. Of these, ES cells, iPS cells, ntES cells, pES cells and the like, which can be obtained by a definite method or prepared easily, are preferable, and particularly, ES cells and iPS cells, for which many scientific findings have been accumulated and which are comparatively widely used since they are suitable for cell banking and the like, are preferable. For autologous transplantation use, iPS cells are preferably used. iPS cells include a cell reprogrammed by a method of introducing a reprogramming factor of nucleic acid, protein and the like into a somatic cell, a method of cultivating a somatic cell in the presence of a specific low-molecular-weight compound, nucleic acid, protein and the like, and the like.

A pluripotent stem cell used for differentiation induction permits easy differentiation induction when seeded in a state close to a single cell. When used as a single cell, however, a human pluripotent stem cell tends to show cell death, and therefore, it is prepared by using an appropriate cell dissociation solution. As the cell dissociation solution, EDTA; protease such as trypsin, collagenase IV, metalloprotease and the like, and the like can be used alone or in an appropriate combination. A cell dissociation solution having low cytotoxicity is preferable, and examples of such cell dissociation solution include commercially available products such as DISPASE (Eidia), TrypLE (Invitrogen), Accutase (MILLIPORE) and the like. Of these, Accutase is preferably used, since it does not show cell death often even when dissociated in a nearly single cell state.

The human pluripotent stem cell used in the present invention is preferably isolated. The "isolation" means that an operation to remove factors other than the object cell or component has been performed, and the object cell or component is in a state not naturally occurring. The purity of the "isolated human pluripotent stem cell" (percentage of human pluripotent stem cells in total cell number) is generally 70% or above, preferably 80% or above, more preferably 90% or above, more preferably 99% or above, most preferably 100%.

The retinal pigment epithelium (RPE) cell is an epithelial cell constituting the retinal pigment epithelium. Whether or not the obtained cell is an RPE cell can be confirmed, for example, by the expression of RPE cell specific gene or a protein, and the like. Examples of the RPE cell specific gene include RPE65, CRALBP, MERTK, BEST1 and the like, and gene expression can be confirmed by RT-PCR and the like. Whether or not the obtained cell has the function of RPE cell can be confirmed by cytokine secretion potency and the like. The cytokine secretion potency can be confirmed by a method of detecting the production amounts of VEGF and PEDF by ELISA and the like. Whether or not the obtained cell is an RPE cell can be judged by the cell morphology (intracellular melanin pigment deposition, polygonal and flat cell morphology, formation of polygonal actin bundle etc.) as an index by using an optical microscope. Unless particularly specified, the RPE cell in the present specification is used to cover an RPE progenitor cell.

In step (a), a feeder cell is not used but a Nodal signal inhibitor and a Wnt signal inhibitor are used to induce differentiation of a human pluripotent stem cell into a pigment cell. The Nodal signal inhibitor and the Wnt signal inhibitor to be contained in a medium (hereinafter to be collectively referred to as a "differentiation inducing factor") are factors inducing differentiation of pluripotent stem cell into RPE cell and those described in WO2005/123902, WO2008/087917, PNAS Aug. 9, 2005 vol. 102 no. 32 11331-11336, Nat Biotechnol. 2008 Feb. 26(2) 215-24, Journal of Cell Science 2009 Sep. 1 122(Pt 17) 3169-79 and the like can be used. The differentiation inducing factor does not need to be contained in the medium throughout the period of step (a), and may be contained in a partial period as long as it can induce differentiation of a human pluripotent stem cell into a pigment cell.

The Nodal signal inhibitor is not particularly limited, as far as it is capable of suppressing Nodal-mediated signal transduction, and protein, nucleic acid, low-molecular-weight compound and the like can be used. As examples of the Nodal signal inhibitor, Lefty-A, Lefty-B, Lefty-1, Lefty-2, soluble Nodal receptor, anti-Nodal antibody, Nodal receptor inhibitor, SB-431542 and the like can be mentioned. Of these, a low-molecular-weight compound is preferable, since it is easily available and shows small variation between lots and, for example, SB-431542 and the like can be used.

The Wnt signal inhibitor is not particularly limited, as far as it is capable of suppressing Wnt-mediated signal transduction, and protein, nucleic acid, low-molecular-weight compound and the like can be used. As examples of the Wnt signal inhibitor, Dkk1, Cerberus protein, Wnt receptor inhibitor, soluble Wnt receptor, Wnt antibody, casein kinase inhibitor, dominant negative Wnt protein, CKI-7 (N-(2-aminoethyl)-5-chloro-isoquinoline-8-sulfonamide), and D4476 (4-{4-(2,3-dihydrobenzo[1,4]dioxyn-6-yl)-5-pyridin-2-yl-1H-imidazol-2-yl}benzamide) can be mentioned. Of these, a low-molecular-weight compound is preferable, since it is easily available and shows small variation between lots. For example, a compound having a selective inhibitory activity on casein kinase I is preferable, and CKI-7, D4476 and the like can be used as such compound.

The medium can be prepared using a medium conventionally used for mammalian cell culture as a basal medium. As the basal medium, for example, one or more kinds of media for mammalian culture, preferably media for pluripotent stem cell culture, can be used in combination. As representative commercially available products, GMEM medium, DMEM medium, DMEM/F12 medium, F10 medium, ReproStem medium (Reprocell) and the like are available, and these may be used in combination or partly modified before use. In step (a), GMEM medium, ReproStem medium (Reprocell) and the like are particularly preferably used.

The medium may contain serum and/or serum alternative. As the serum, a serum derived from a mammal such as bovine and the like can be used, and fetal bovine serum (FBS) and the like are generally used. When culture aims at autologous transplantation, the patient's own serum can also be used. The serum alternative is a low-protein replacement used instead of a serum such as FBS and the like used for cell culture. As commercially available products, for example, knockout Serum Replacement (KSR), Chemically-defined Lipid concentrated (manufactured by Gibco), Glutamax (manufactured by Gibco) and the like, and N2 and B27, which are serum alternatives for nerve cell culture, and the like are available.

In one embodiment, a serum-free medium is used as a medium for step (a). A serum-free medium means a medium free of a plain or unrefined serum, and media containing purified blood-derived components and animal tissue-derived components (for example, growth factor) fall under the serum-free medium. A serum-free medium is used in combination with a serum alternative and, as such serum alternative, KSR and the like are preferably used.

The concentration of serum or serum alternative can be appropriately set within the range of, for example, 0.5-30% (v/v). The concentration may be constant or stepwisely changed and, for example, the concentration may be stepwisely decreased at about 1-3 day (preferably 2 day) intervals. For example, serum or serum alternative can be added at three-step concentrations of 20%, 15% and 10%.

The medium can contain a Rho kinase inhibitor. For example, addition of a Rho kinase inhibitor for a predetermined period from immediately after the start of differentiation induction is preferable, since the cell death of human pluripotent stem cells dispersed in a culture medium can be suppressed to avoid decrease in the cell number. While the Rho kinase inhibitor is not particularly limited, for example, Y-27632 and the like can be used. A Rho kinase inhibitor may be added, for example, for the entire period of differentiation induction step, or only a partial period as long as differentiation of a human pluripotent stem cell into a pigment cell can be induced. In step (a), after adhesion of the seeded pluripotent stem cells, the cells that have not been differentiated into RPE cell may be detached and dispersed in the medium, and the death of such unnecessary cells had better not be prevented. Therefore, after adhesion of the seeded cells to a culture vessel, the Rho kinase inhibitor is preferably removed from the medium.

The medium can contain other additives generally used for culture of mammalian cells, in addition to the aforementioned basal medium, serum and/or serum alternative, differentiation inducing factor and Rho kinase inhibitor. The additives are not particularly limited as long as RPE cell can be produced by the method of the present invention. For example, growth factor (for example, insulin etc.), iron source (for example, transferrin etc.), mineral (for example, sodium selenate etc.), saccharides (for example, glucose etc.), organic acid (for example, pyruvic acid, lactic acid etc.), serum protein (for example, albumin etc.), amino acid (for example, L-glutamine etc.), reducing agent (for example, 2-mercaptoethanol etc.), vitamins (for example, ascorbic acid, d-biotin etc.), antibiotic (for example, streptomycin, penicillin, gentamicin etc.), buffer (for example, HEPES etc.) and the like can be mentioned. Such additives are preferably contained within the concentration range known per se.

In step (a), differentiation induction from a pluripotent stem cell to a pigment cell is performed by adhesion culture. When the cells are adhered to a culture vessel during differentiation induction, the cells are not lost easily by medium exchange, and therefore, floating culture is more preferable. Adhesion culture can be performed by using a cell-adhesive culture vessel. While the cell-adhesive culture vessel is not particularly limited as long as the surface of the culture vessel is treated to improve adhesiveness to the cell, for example, a culture vessel having a coated layer containing an extracellular matrix, a synthetic polymer and the like can be used. The coated layer may be constituted with one or more kinds of components, or may be formed by a single layer or multiple layers. While the extracellular matrix is not particularly limited as long as it can form a coated layer showing adhesiveness to a pluripotent stem cell, for example, collagen, gelatin, laminin, fibronectin and the like can be mentioned, which can be used alone or in combination. As a commercially available product containing multiple kinds of extracellular matrices, Matrigel (BD), CELL-Start (Invitrogen) and the like are available. As the synthetic polymer, biologically or chemically produced ones can be used. For example, cationic polymers such as polylysine (poly-D-lysine, poly-L-lysine), polyornithinepolyethyleneimine (PEI), poly-N-propylacrylamide (PIPAAm) and the like are preferably used. These extracellular matrix, synthetic polymer and the like may be biologically produced by using bacterium, cells and the like and introducing genetic modification as necessary, or chemically synthesized.

Particularly, for use for the preparation of a cell to be transplanted, a clinically available material with less cytotoxicity can be preferably used. For example, a culture vessel wherein a coated layer containing gelatin is formed as a single layer or in combination with other layer can be used. When combined with other layer, a coated layer containing gelatin is preferably formed on the surface to be in direct contact with the cell. Particularly, it is preferable to use a culture vessel coated with gelatin and polylysine, since many pigment cells obtained by differentiation induction are spherical cells having smooth surface, to which unnecessary cells do not attach easily, and unnecessary cells are easily detached from the RPE cells in the subsequent step (c) to facilitate isolation and purification of the RPE cells. More preferably, a culture vessel coated with gelatin and polylysine wherein the surface to be in direct contact with the cell is a gelatin-coated layer is used.

Other culture conditions such as culture temperature and $CO_2$ concentration in the culture can be set as appropriate. Culture temperature is not particularly limited, and is, for example, about 30 to 40° C., preferably about 37° C. The $CO_2$ concentration is, for example, about 1 to 10%, preferably about 5%.

One example of the embodiment of step (a) is shown below. Human pluripotent stem cells are cultured in a medium containing Y-27632, SB431542 and CKI-7 on a gelatin-coated culture dish under the conditions of 37° C., 5% $CO_2$ for 1 day (Day 0). The next day (Day 1), a half amount of the medium is exchanged with GMEM medium containing 20% KSR, Y-27632, SB431542 and CKI-7. Further, 2 days later (Day 3), the same operation is repeated. Further, 2, 4, 6 days later (Day 5, 7, 9), a half amount of the medium is exchanged with GMEM medium containing 15% KSR, Y-27632, SB431542 and CKI-7. Further, 2 days later (Day 11), a half amount of the medium is exchanged with GMEM medium containing 10% KSR, Y-27632, SB431542 and CKI-7. Further, 2, 4, 6 days later (Day 13, 15, 17), a half amount of the medium is exchanged with GMEM medium containing 10% KSR, SB431542 and CKI-7. Thereafter (Day 19 ff.), the total amount of the medium is exchanged every other day with GMEM medium containing 10% KSR until a colony of RPE cell with brown-black pigment emerges. On Day 21-28, a colony of pigment cells starts appearing.

In step (a), cultivation is performed until emergence of pigment cells and a culture containing the pigment cells is obtained. Culture is a product obtained by cultivation of a cell, and contains cell, medium and the like. The emergence of a pigment cell can be confirmed by confirming the presence of a cell in brown-black by an optical microscope. According to the present invention, pigment cells can emerge on day 21-28 from the start of cultivation as mentioned above. On the other hand, the SFEB/CS method that induces differentiation by floating culture requires 40 days of culture time before emergence of pigment cells (Journal of Cell Science 2009 Sep. 1 122(Pt 17) 3169-79). Therefore, the method of the present invention is extremely useful as a method capable of drastically shortening the time from the start of the differentiation induction of pluripotent stem cells to the emergence of pigment cells.

When the emergence of pigment cells is confirmed in step (a), cultivation is performed under the conditions of step (b).

Step (b) Maturation Step

In step (b), the culture containing the pigment cell obtained in the aforementioned step (a) is subjected to adhesion culture, and a culture containing a colony of pigment cells is obtained. In step (b), differentiation into a pigment cell started in step (a) is further continued to promote pigment cell growth, whereby a colony of pigment cells is formed. The medium in step (b) can be prepared by using the basal medium, serum, serum alternative exemplified as being usable for the adhesion culture in step (a). In step (b), a medium different from that in step (a) can be used. For example, a medium suitable for maintenance culture of RPE cells (RPE maintenance medium) can be utilized. Examples of the RPE maintenance medium include a medium containing DMEM, DMEM/F12, F10 medium and the like as a basal medium, and serum such as FBS and the like or serum alternative for nerve cell culture, such as B27 and the like, preferably B27, as serum or serum alternative. In step (b), the concentration of serum or serum alternative is preferably constant and, for example, about 0.5-20%.

The medium in step (b) can contain, besides the aforementioned basal medium, serum and/or serum alternative, other additives generally used for culture of mammalian cell. As the additive, those recited as additives used in step (a) can be mentioned. For the medium in step (b), addition of a differentiation inducing factor and a Rho kinase inhibitor used in step (a) is not required.

Also, other culture conditions such as culture temperature and $CO_2$ concentration in the adhesion culture can be set as appropriate as in step (a).

The culture obtained step (b) contains a colony of pigment cells. The pigment cell in the colony contains a differentiated RPE cell having a pigment. The RPE cell having a pigment is a cell having a proliferative capacity, and can be further grown by isolating enzymatically or physically and placing the cell in a new culture system.

Cultivation in step (b) is continued until a colony of pigment cells emerges. The emergence of the colony of pigment cells can be confirmed by an optical microscope. While the culture period of step (b) is not limited as long as a colony of pigment cells can be formed, it is generally about 1-3 weeks.

In step (b), when a colony of pigment cells is formed in a culture vessel and the pigment becomes dark, cultivation is performed under the conditions of step (c).

Step (c) Cultivation of RPE Cells

In step (c), the pigment cell is isolated from the culture obtained in step (b) and cultured to give an RPE cell.

The isolation of pigment cell in step (c) can be performed by a known method, for example, by selectively collecting a cell having the morphology and color same as those of RPE cell (typically, a cell showing intracellular melanin pigment deposition, polygonal and flat cell morphology, formation of polygonal actin bundle) under an optical microscope, using pipette chip, capillary and the like. That is, the cell isolated in step (c) is preferably an RPE cell having a pigment. By growing the isolated cell by subjecting to cultivation, RPE cells in a desired cell amount and in a desired maturation degree can be obtained.

For cultivation of the isolated pigment cell, the conditions and method known as a cultivation method of RPE cell can be applied. For example, cultivation can be performed by a method including floating culture, adhesion culture or a combination thereof and using the RPE maintenance medium exemplified in step (b).

Other culture conditions such as culture temperature and $CO_2$ concentration and the like for the cultivation can be set as appropriate as in step (a).

In one embodiment, substantially purified RPE cells can be obtained in step (c). The "substantially purified RPE cells" means that the proportion of the number of RPE cells contained in the cell population is 95% or above, preferably 99% or above, most preferably 100%.

Step (c) comprises, for example, (c-1) a step of subjecting the culture obtained in step (b), which contains a colony of pigment cells, to floating culture to obtain a floating aggregate, and (c-2) a step of isolating the pigment cell from the obtained floating aggregate, subjecting the pigment cell to adhesion culture, and passaging the pigment cell selectively to give an RPE cell.

Step (c-1) Floating Culture of RPE Cells

In step (c-1), a culture containing the colony of pigment cells obtained in step (b) is subjected to floating culture. The floating culture means that cells having assembled and formed an aggregate (floating aggregate) are cultured in a floating state in a culture medium. In step (c-1), pigment cells (preferably, RPE cells containing a pigment) form a floating aggregate, and unnecessary cells other than the pigment cells (preferably, RPE cells containing a pigment) are detached and fall off in the medium without being included in the floating aggregate. Therefore, unnecessary cells other than the pigment cells (preferably, RPE cells containing a pigment) can be removed easily without any special operation other than the floating culture, and the purity of the pigment cells (preferably, RPE cells containing a pigment) can be increased.

A cell population containing the pigment cells can be recovered by, for example, treating the culture obtained in step (b) with a cell dissociation solution, and detaching the cells adhered to the culture vessel with a scraper. While the cell dissociation solution is not particularly limited, EDTA; protease such as trypsin, collagenase IV, metalloprotease; and the like can be used alone or in an appropriate combination. Of these, one with less cellular cytotoxicity is preferable. As such cell dissociation solution, for example, commercially available products such as DISPASE (Eidia), TrypLE (Invitrogen), Accutase (MILLIPORE) and the like are available. To facilitate formation of a floating aggregate, the cells to be subjected to floating culture preferably form a certain level of aggregation. From such aspect, DISPASEII is preferably used since it has an appropriate dissociation activity.

In step (c-1), a medium described in step (b) can be used.

The floating culture in step (c-1) can be performed in a non-cell-adhesive culture vessel. The non-cell-adhesive culture vessel is not particularly limited as long as it has a surface made from a material free of adhesiveness to the cell or it has been treated to reduce adhesiveness to the cell. For example, a culture vessel other than those exemplified as the cell-adhesive culture vessels in step (a) can be used. As the culture vessel having a surface made from a material free of adhesiveness to the cell, for example, a culture vessel for bacterium culture and the like can be used, and as the culture vessel that has been treated to reduce adhesiveness to the cell, for example, commercially available products such as a culture vessel coated with a cell non-adhesive polymer (e.g., 2-methacryloyloxyethyl phosphorylcholine (MPC) polymer and the like) and the like can be used.

Other culture conditions such as culture temperature and $CO_2$ concentration and the like for the cultivation can be set as appropriate as in step (a).

When a floating aggregate containing pigment cells (preferably, RPE cells containing a pigment) is formed and unnecessary cells other than the pigment cells (preferably, RPE cells containing a pigment) are sufficiently detached and fall off in step (c-1), culture is performed under the conditions of step (c-2).

Step (c-2) Adhesion Culture of RPE Cells

In step (c-2), the pigment cells (preferably, RPE cells containing a pigment) are isolated from the floating aggregate obtained in step (c-1), subjected to adhesion culture, and selectively passaged to give RPE cells. In step (c-2), a colony of the pigment cells (preferably, RPE cells containing a pigment) is selectively passaged to achieve purification and proliferation of these cells, whereby a sufficient number of highly pure RPE cells can be acquired.

In one embodiment, substantially purified RPE cells can be obtained in step (c-2). The "substantially purified RPE cells" means that the proportion of the number of RPE cells contained in the cell population is not less than 95%, preferably not less than 99%, most preferably 100%.

The isolation of pigment cells (preferably, RPE cells containing a pigment) in step (c-2) is performed, for example, by selective collection based on morphology and pigment as indices under an optical microscope. To be specific, the morphology and pigment of the cells constituting the floating aggregate are observed under an optical microscope, a floating aggregate of pigment cells containing cells in different colors such as white, yellow and the like is avoided, and only a colony consisting of pigment cells free of unnecessary cells (typically, a colony consisting of cells showing intracellular melanin pigment deposition, polygonal and flat cell morphology, formation of polygonal actin bundle) is picked up.

In step (c-2), a medium described in step (b) can be used. The medium for step (c-2) can promote adhesion of cell particularly by adding FBS from the start of cultivation and removing FBS on day 3.

The medium for step (c-2) can contain, for example, a growth factor such as FGF and the like, a Nodal signal inhibitor such as SB-431542 and the like, and the like. FGF can be used to promote cell proliferation. FGF may be added over the entire period of step (c-2) or a part thereof. For example, FGF may be added after adhesion of the cell to the culture vessel. SB-431542 may be added over the entire period of step (c-2) or a part thereof in order to retain property of the RPE cell. In one embodiment, SB-431542 is added after completion of the first passage. The concentration of FGF is, for example, about 1-30 ng/ml, preferably about 5-20 ng/ml. The concentration of SB-431542 is, for example, about 0.01-5 µM, preferably about 0.1-2 µM.

The adhesion culture in step (c-2) can be performed using the cell-adhesive culture vessel exemplified in step (a). The cell-adhesive culture vessel is not particularly limited as long as it has adhesiveness to the RPE cell, and a culture vessel usable for the adhesion culture in step (a) can be used, and a culture vessel coated with CELLStart (Invitrogen) is preferably used.

Other culture conditions such as culture temperature and $CO_2$ concentration and the like in the culture can be set as appropriate as in step (a).

At the time point when the pigment cells (preferably, RPE cells containing a pigment) isolated from the floating aggregate have adhered to a culture vessel and become confluent, the first passage is conducted.

A method of selective passage of the colony of pigment cells (preferably, RPE cells containing a pigment) includes a method comprising selectively collecting, under an optical microscope, cells having morphology and color tone same as those of RPE cell (typically, cells showing intracellular melanin pigment deposition, polygonal and flat cell morphology, formation of polygonal actin bundle) by using a pipette tip, capillary and the like, adjusting appropriate cell concentration and seeding them again. To be specific, umbonal cells and yellow, spherical cells contaminating the RPE cells are scraped off with the tip of a pipette, outer abnormal pigment cells with enlarged morphology are further scraped off to selectively leave a colony of uniform RPE cells, after which the cells are detached with the cell dissociation solution exemplified above, completely dispersed, and seeded at a cell concentration of 2-4×10$^5$ cells/ml to perform adhesion culture. While the passage number is not particularly limited, for example, the cells can be passaged 1 to 4 times, preferably 1 or 2 times. By passaging, a retinal pigment epithelial cell population having high purity (preferably, substantially purified retinal pigment epithelial cells) can be obtained.

By continuing culture even after passaged cells became confluent, polygonal, light brown cells can be obtained as the RPE cells.

According to the production method of RPE cells of the present invention, differentiation from pluripotent stem cell can be induced without using feeder cells and a culture supernatant thereof. Therefore, the method is superior in safety, can simplify the working process, and shows less variation of differentiation induction efficiency between cells. Furthermore, since differentiation is induced by adhesion culture, the period for producing RPE cells can be drastically shortened, and the production cost can be suppressed. Furthermore, since unnecessary cells can be easily removed by the use of a specific culture vessel, work efficiency can be improved and a highly pure RPE cell population can be conveniently produced.

Treatment Method

Moreover, the present invention provides a method of treating a retinal disease in a human, comprising administering a therapeutically effective amount of retinal pigment epithelial cells produced by the above-mentioned method to the human. Examples of such retinal disease include a disease showing dysfunction or atrophy of the pigment epithelium due to a genetic factor, a disease showing secondary dysfunction or atrophy of the pigment epithelium due to an inflammatory disease and the like, all diseases associated with choroidal neovascularization due to a disorder in the pigment epithelium and the like. Representative examples of the retinal disease include age-related macular degeneration, angioid streaks, high myopia (degenerative myopia), idiopathic neovascular maculopathy, retinitis pigmentosa, Stargardt's disease, Best's disease, choroideremia and the like. The cells produced by the above-mentioned method may be administered as a suspension or may be transplanted as a cell sheet. The cell transplantation can be performed according to a known method by using, for example, about 10$^5$ cells as the cells to be transplanted and a tool capable of subretinal injection.

The cells obtained by the method of the present invention are morphologically and functionally equivalent to the RPE cells in the body, and therefore, they can be utilized for various applications besides transplantation use and can be used, for example, for retinal toxicity test and the like.

The contents disclosed in any publication cited in the present specification, including patents and patent applications, are hereby incorporated in their entireties by reference, to the extent that they have been disclosed herein.

The present invention is explained in more detail in the following by referring to Examples, which are not to be construed as limitative.

EXAMPLES

Example 1 Production of iPS Cell-Derived RPE Cells—1 Reagent

The test was performed using reagents having the following composition.

Dissociation solution for iPS cell (PBS (Invitrogen), 0.25% trypsin (Invitrogen), 1 mg/ml collagenase IV (Invitrogen), 20% KSR (Invitrogen), 1 mM calcium chloride (Otsuka Pharmaceutical Co., Ltd.))

Basal medium (GMEM medium (Invitrogen), KSR (Invitrogen), 0.1 mM MEM non-essential amino acid solution (INVITROGEN), 1 mM sodium pyruvate (SIGMA), 0.1 M 2-mercaptoethanol (Wako Pure—Chemical Industries, Ltd.), 100 U/ml penicillin-100 µg/ml streptomycin (Invitrogen))

Primary differentiation induction medium (ReproStem medium (Reprocell), 10 µM Y-27632 (Wako Pure Chemical Industries, Ltd.), 5 µM SB431542 (SIGMA), 3 µM CKI-7 (SIGMA))

Secondary differentiation induction medium (differentiation induction medium containing 20% KSR, 10 µM Y-27632 (Wako Pure Chemical Industries, Ltd.), 5 µM SB431542 (SIGMA), 3 µM CKI-7 (SIGMA))

Tertiary differentiation induction medium (basal medium containing 15% KSR, 10 µM Y-27632 (Wako Pure Chemical Industries, Ltd.), 5 µM SB431542 (SIGMA), 3 µM CKI-7 (SIGMA))

Quaternary differentiation induction medium (basal medium containing 10% KSR, 10 µM Y-27632 (Wako Pure Chemical Industries, Ltd.), 5 µM SB431542 (SIGMA), 3 µM CKI-7 (SIGMA))

Quinary differentiation induction medium (basal medium containing 10% KSR, 5 µM SB431542 (SIGMA), 3 µM CKI-7 (SIGMA))

Senary differentiation induction medium (basal medium containing 10% KSR)

RPE maintenance medium (67% DMEM low glucose (SIGMA), 29% F12 (SIGMA), 1.9 mM L-glutamine (Invitrogen), 1.9% B-27 supplement (Invitrogen), 96 U/mL penicillin sodium, 96 µg/ml streptomycin sulfate)

Preparation of iPS Cells

According to the method described in Takahashi et al. (Cell, 2007; 131: 861-872), human iPS cell lines (59M8, K31M28, K11PD17, K21S4, K10M15, 101M6, K32M17) were prepared by introducing reprogramming factors (human Oct3/4, Sox2, Klf4, c-Myc) into human skin-derived fibroblasts by using a retrovirus. According to the method described in Fusaki et al. (Proc Jpn Aced Ser B Phys Biol Sci. 2009 85(8)348-62), human iPS cell lines (59SCV3, 59SV4, 59SV9) were prepared by introducing reprogramming factors (human Oct3/4, Sox2, Klf4, c-Myc) into human skin-derived fibroblasts by using a Sendai virus. According to the method described in Okita et al. (Nat Methods. 2011 May; 8(5): 409-12), human iPS cell lines (K21EV15, 101EV3, K11EV9) were prepared by introducing reprogramming factors (human Oct3/4, Sox2, Klf4, L-Myc, LIN28) into human skin-derived fibroblasts by using a plasmid vector.

Differentiation Induction Step

The obtained human iPS cells were each detached with a dissociation solution for IPS cell, suspended in ReproStem medium (Reprocell), and dissociated into aggregates of about 10-20 cells by pipetting. The obtained cultures were cultured in a primary differentiation induction medium (ReproStem medium added with differentiation inducing factors) on a culture dish (BD FALCON) coated with 0.1% gelatin (SIGMA) solution, under the conditions of 37° C., 5% CO$_2$ for 1 day. On Day 1 and Day 3, a half amount of the medium was exchanged with a secondary differentiation induction medium (20% KSR). Further, a half amount of the medium was exchanged with Tertiary differentiation induction medium (15% KSR) on Days 5, 7, 9, a half amount of the medium was exchanged with Quaternary differentiation induction medium (10% KSR) on Day 11 and a half amount of the medium was exchanged with Quinary differentiation induction medium (10% KSR, Y-27632 free) on Days 13, 15, 17. From Day 19, the medium was exchanged with Senary differentiation induction medium every other day. The cells did not form a floating aggregate observed in conventional differentiation induction methods (SFEB method), but gradually started to adhere to the culture dish simultaneously with the start of the differentiation induction, 70-80% of the cells adhered on Day 10, and almost all the cells adhered to the culture dish on around Day 20 to form a sheet-like multi-layer population. A colony of RPE cells having a pigment appeared on Day 21-28.

On the other hand, the pigment cells appeared on Day 40 by a conventional SFEB method wherein differentiation induction was performed by culturing floating aggregates. In comparison therewith, the method of the present invention could markedly shorten the differentiation induction period.

Mature Step

At the time point when colonies of RPE cells having a pigment appeared, the medium was exchanged with RPE maintenance medium, and thereafter up to Day 40, the total amount of the medium was exchanged with RPE maintenance medium every 3-4 days. The pigment in the cell became darker as the cultivation proceeded. On Day 40, many colonies of RPE cells having a dark pigment were confirmed.

Culture of RPE Cells

The pigment cells were isolated from the culture on Day 40, and cultured according to a method known as a cultivation method of RPE cell, whereby sheet-like cells comprising brown cells was obtained.

Example 2 Production of iPS Cell-Derived RPE Cells—2 Reagent

Reagent having the following composition was used.
Dissociation solution for RPE cell (PBS (Invitrogen), 0.25% trypsin (Invitrogen), 1 mg/ml collagenase IV (Invitrogen), 20% KSR, 1 mM calcium chloride (Otsuka Pharmaceutical Co., Ltd.))

RPE maintenance medium (67% DMEM low glucose (SIGMA), 29% F12 (SIGMA), 1.9 mM L-glutamine (Invitrogen), 1.9% B-27 supplement (Invitrogen), 96 U/mL penicillin sodium, 96 µg/mL streptomycin sulfate)

RPE adhesion medium (37% F-12, 34% DMEM low glucose, 22% DMEM high glucose, 5% FBS, 0.96% B-27 additive, 0.96 mM L-glutamine, 98 U/mL benzylpenicillin sodium, 98 µg/mL streptomycin sulfate)

Primary RPE culture medium (RPE maintenance medium, 10 ng/ml bFGF)

Secondary RPE culture medium (RPE maintenance medium, 10 ng/ml bFGF, 0.5 µM SB431542)

Culture of RPE Cell

1. Purification by Floating Culture

To the culture on Day 40 obtained in Example 1 was added a dissociation solution for RPE cell, and the cells were detached with a scraper. The detached cells were placed in a tube and incubated at 37° C. for 40 min (vortexed every 5-10 min). After washing 3 times with RPE maintenance medium, the cells were seeded in an RPE maintenance medium in a non-adhesive culture dish (NUNC) to start floating culture. The aggregates in the colony of pigment cells grew during the floating culture. With the passage of time, the cells other than the pigment cells were detached and fell off from the aggregates of the pigment cells. The cells were purified in 10-14 days from the start of the culture.

2. Purification by Subculture

Brown-black colonies of pigment cells were selectively picked up from the obtained culture under an optical microscope. Colonies containing cells with different pigment such as white, yellow and the like were excluded from the pick-up target. The colonies were seeded in an RPE adhesion medium on a culture dish coated with CELLstart (Invitrogen) for a primary passage (P1). On day 3, the cells were washed once with RPE maintenance medium, and the medium was changed to primary RPE culture medium. On day 7, the medium was changed again to the primary RPE culture medium and the cultivation was continued. As a result, the cells increased to a sufficient amount in 10-14 days from the seeding.

Umbonal cells and yellow, spherical cells contaminating the RPE cells were scraped off from the obtained culture with the tip of a pipette under an optical microscope. RPE cells that have grown morphologically too large were further scraped off to selectively leave uniform RPE cells. The cells were detached and dispersed with 0.25% trypsin-EDTA and seeded at a cell concentration of about $2-4\times10^5$ cells/ml in RPE adhesion medium on a culture dish coated with CELLstart (Invitrogen). On day 2, the cells were washed once with RPE maintenance medium, and the medium was changed to secondary RPE culture medium. The medium was changed every 2 or 3 days and culture was continued. As a result, the cells became confluent in 4-5 days after seeding, and polygonal, light brown pigment cells were obtained on day 14-21.

(Evaluation 1) Expression of RPE Cell Markers

The obtained pigment cells were subjected to RT-PCR analysis according to the method described in Journal of Cell Science 2009 Sep. 1 122(Pt 17) 3169-79 with the primers having the following sequences. As a result, expression of RPE cell specific genes (RPE65, CRALBP, MERTK, BEST1) of the same level as commercially available human RPE cell line was observed, based on which the cells were confirmed to be RPE cells.

```
                                    (SEQ ID NO: 1)
RPE65-F     TCC CCA ATA CAA CTG CCA CT (SEQ ID NO: 2)
RPE65-R     CCT TGG CAT TCA GAA TCA GG (SEQ ID NO: 3)
CRALBP-F    GAG GGT GCA AGA GAA GGA CA (SEQ ID NO: 4)
CRALBP-R    TGC AGA AGC CAT TGA TTT GA (SEQ ID NO: 5)
MERTK-F     TCC TTG GCC ATC AGA AAA AG (SEQ ID NO: 6)
MERTK-R     CAT TTG GGT GGC TGA AGT CT (SEQ ID NO: 7)
BEST1-F     TAG AAC CAT CAG CGC CGT C (SEQ ID NO: 8)
BEST1-R     TGA GTG TAG TGT GTA TGT TGG
```

(Evaluation 2) Cytokine Secretion Potency

The obtained pigment cells were examined by ELISA for the production amounts of VEGF and PEDF according to the method described in Arvydas M, IOVS.2006; 47: 3612-3624. As a result, the presence of cytokine secretion potency of the same level as the RPE cells of adult retina was confirmed.

Comparative Example 1

In the same manner as in Example 1 except that floating culture was performed in the differentiation induction step by using an MPC-treated non-adhesive culture dish (Nunc) instead of the culture dish (BD FALCON) coated with 0.1% gelatin (SIGMA) solution, a differentiation induction step was performed.

As a result, appearance of pigment cells was confirmed on Day 40 in the differentiation induction step, which took about 2 times longer time than in Example 1.

Example 2

In the same manner as in Example 1 except that a poly-D-lysine/gelatin-coated culture dish (prepared by coating poly-D-lysine-coated culture dish (BD FALCON) with 0.1% gelatin (SIGMA) solution) was used instead of the culture dish (BD FALCON) coated with 0.1% gelatin (SIGMA) solution in the differentiation induction step of human iPS cell line (K10M15), RPE cells were produced.

As a result, as compared to Example 1, the proportion of the umbonal cells contaminating a colony of pigment cells obtained by differentiation induction markedly decreased, and spherical pigment cells having smooth surface were formed highly frequently. Possibly because the pigment cells have a smooth surface to which unnecessary cells are difficult to attach, unnecessary cells were easily detached from a colony of pigment cells in the subsequent purification step by floating culture, selective pick-up in the purification step by subculture could be performed with ease, and work efficiency was markedly improved.

INDUSTRIAL APPLICABILITY

According to the production method of the present invention, differentiation into RPE cell can be induced without using feeder cells and a culture supernatant thereof. Therefore, the method is superior in safety, can simplify the working process, and shows less variation of differentiation induction efficiency between cells. Furthermore, since differentiation is induced by adhesion culture, the period for producing RPE cells can be drastically shortened, and the production cost can be suppressed. The RPE cells produced by the production method of the present invention is useful for the treatment of a retinal disease.

The invention claimed is:

1. A method of producing a retinal pigment epithelial cell from a human pluripotent stem cell, which comprises
   (a) a step of providing isolated human pluripotent stem cells, wherein the isolated human pluripotent stem cells are dispersed by a cell dissociation solution,
   (b) a step of inducing differentiation of the isolated human pluripotent stem cells into pigment cells by adhesion cultivation of the isolated and dispersed human pluripotent stem cells of step (a) in a medium containing a Nodal signal inhibitor and a Wnt signal inhibitor at a concentration sufficient to induce differentiation of the human pluripotent stem cells into pigment cells in the absence of feeder cells to yield a culture containing the pigment cells,
   (c) a step of subjecting the obtained culture of step (b) to further adhesion culture to yield a culture containing a pigment cell colony, and
   (d) a step of isolating the pigment cell from the obtained culture of step (c) and culturing the cell to yield the retinal pigment epithelial cell.

2. The method according to claim 1, wherein the adhesion culture in step (b) is performed using a culture vessel coated with gelatin, or a culture vessel coated with polylysine and gelatin.

3. The method according to claim 1, wherein the Nodal signal inhibitor is SB-431542, and the Wnt signal inhibitor is CKI-7.

4. The method according to claim 1, further comprising adding a serum and/or a serum alternative while stepwise reducing the concentration(s) thereof in step (b).

5. The method according to claim 1, wherein the medium in step (b) is a serum-free medium.

6. The method according to claim 1, wherein step (d) comprises
   (d-1) a step of subjecting the obtained culture of step (c) to floating culture and
   (d-2) a step of isolating the pigment cell from the obtained floating aggregate, subjecting the pigment cell to adhesion culture, and to selective passage to give a retinal pigment epithelial cell.

7. The method according to claim 1, wherein the adhesion cultivation in step (b) is performed by using a culture vessel having a coated layer containing an extracellular matrix.

* * * * *